(12) United States Patent
Lee et al.

(10) Patent No.: US 7,732,191 B2
(45) Date of Patent: Jun. 8, 2010

(54) HYBRIDIZATION SYSTEM USING THE CONTROL OF PUMP AND VALVES IN CLOSED SYSTEM

(75) Inventors: Soo-suk Lee, Suwon-si (KR); Sung-ouk Jung, Suwon-si (KR); Chang-eun Yoo, Seoul (KR); Hun-joo Lee, Seoul (KR); Christopher Hansung Ko, Seongnam-si (KR); Nam Huh, Seoul (KR)

(73) Assignee: Samsung Electronics Co., Ltd. (KR)

( * ) Notice: Subject to any disclaimer, the term of this patent is extended or adjusted under 35 U.S.C. 154(b) by 1218 days.

(21) Appl. No.: 11/295,843

(22) Filed: Dec. 6, 2005

(65) Prior Publication Data

US 2006/0154360 A1 Jul. 13, 2006

(30) Foreign Application Priority Data

Dec. 6, 2004 (KR) .................. 10-2004-0101654

(51) Int. Cl.
*C12M 1/34* (2006.01)
*C12M 1/36* (2006.01)
(52) U.S. Cl. .............. 435/287.2; 435/286.5; 435/286.6; 435/286.7; 435/288.3; 435/293.1; 422/130
(58) Field of Classification Search .............. 435/286.5, 435/287.2, 293.1, 286.6, 286.7, 288.3; 422/130
See application file for complete search history.

(56) References Cited

U.S. PATENT DOCUMENTS

| | | | | |
|---|---|---|---|---|
| 5,273,905 A | * | 12/1993 | Muller et al. ............. | 435/286.5 |
| 6,391,623 B1 | | 5/2002 | Besemer et al. | |
| 6,432,696 B2 | | 8/2002 | Custance et al. .......... | 435/287.2 |
| 6,432,969 B1 | | 8/2002 | Villhauer | |
| 2003/0013184 A1 | | 1/2003 | Streit et al. .............. | 435/287.2 |
| 2003/0087292 A1 | | 5/2003 | Chen et al. | |
| 2004/0101870 A1 | | 5/2004 | Caubet et al. | |

FOREIGN PATENT DOCUMENTS

| | | |
|---|---|---|
| WO | 02/072264 A1 | 9/2002 |
| WO | 03/015922 A1 | 2/2003 |

(Continued)

OTHER PUBLICATIONS

Taiwan Office Action with English Translation dated Aug. 4, 2008 for Patent Application No. 094142370.

(Continued)

*Primary Examiner*—William H Beisner
(74) *Attorney, Agent, or Firm*—Cantor Colburn LLP

(57) ABSTRACT

Provided is a hybridization system for hybridizing a biochip including: a chamber device including at least a hybridization chamber including a support for a biochip and a first cover having a sample inlet; an agitation device including: two air channels connected to ends of the hybridization chamber; two valves disposed in the air channels; an integrated air channel to which the two air channels are connected; and an air pump disposed in the integrated air channel; and a washing and drying device including: a flow channel connected to one of the two air channels through a branched valve; a flow pump disposed in the flow channel; and a buffer inlet disposed opposite the flow channel.

15 Claims, 22 Drawing Sheets

FOREIGN PATENT DOCUMENTS

WO 03/015923 A1 2/2003

OTHER PUBLICATIONS

Partial European Search Report for EP 05 02 6633 dated Jun. 5, 2009.

European Search Report for Application No. 05026633.7-1270/1666887 dated Sep. 10, 2009.

Chinese Office action dated Dec. 21, 2007 with English Translation.

* cited by examiner

Prior Art

Prior Art

Prior Art

Prior Art

Prior Art

Prior Art

Prior Art

Prior Art

Prior Art

HYBRIDIZATION SYSTEM USING THE CONTROL OF PUMP AND VALVES IN CLOSED SYSTEM

CROSS-REFERENCE TO RELATED PATENT APPLICATIONS

This application claims the benefit of Korean Patent Application No. 10-2004-0101654, filed on Dec. 6, 2004, in the Korean Intellectual Property Office, the disclosure of which is incorporated herein in its entirety by reference.

BACKGROUND OF THE INVENTION

1. Field of the Invention

The present invention relates to a hybridization system, and more particularly, to a hybridization system in which operations for hybridization of a biochip, such as sample diffusing, sample agitating, chip washing, and chip drying are automized.

2. Description of the Related Art

A biochip is formed by affixing on a support a bimolecular probe to be analyzed with high density. The biomolecular probe may be DNA, protein, or the like. By detecting whether the probe is hybridized with a target material contained in a sample, gene expression characteristics, genetic defects, protein distribution, reaction characteristics, or the like can be analyzed. Biochips are categorized into DNA chips, protein chips, and the like according to the type of probes used. In addition, biochips are categorized into micro-array chips affixed on solid supports and lab-on-a-chips affixed on microchannels according to affixed subjects. Biochips require a hybridization chamber, an agitation system, and a washing/drying system to attain effective hybridization between the target materials contained in the sample and the probe.

Conventionally, hybridization is manually performed in a hybridization chamber formed between a slide glass and a cover glass illustrated in FIG. 1. This results in variations in experimental conditions according to users, a long testing time of 16 to 17 hours, and the requirement of up to 100 μl or less of a sample.

In order to overcome these disadvantages, an automatic system in which hybridization, washing, and drying are automatically performed has been developed. The use of the automatic system using fluctuation results in an increase of hybridization efficiency, a decrease in variations among users, a short testing time of 2 hours or less, and the requirement of only up to 50 μl or less of a sample.

FIGS. 2A and 2B are views of a conventional automatic hybridization system developed by Affymetrix Co. disclosed in U.S. Pat. No. 6,391,623. Referring to FIGS. 2A and 2B, a hybridization chamber is connected to a pump by a fluid delivery system, and hybridization is facilitated by the circulation of a fluid. In addition, sample loading, agitation, washing, and drying are performed in a single system. However, for this apparatus, a large amount of the sample is needed due to the use of a peristaltic pump and a circulation fluid channel. Because of this, after hybridization is performed for 16 hours, the DNA chip is washed and dried using a rotary oven. In addition, only the chip obtained from Affymetrix Co can be used in the cartridge, that is, this apparatus is incompatible.

FIGS. 3A and 3B are views of a conventional automatic hybridization system developed by Tecan Co. disclosed in US 20030013184. Referring to FIGS. 3A and 3B, the agitation of the solution and drying of a slide are performed on a board, and after the sample is injected, hybridization, washing, and drying are automatically performed. Two ends of a hybridization chamber are connected to two channels, and each of the channels includes a membrane for agitation and two micro pumps to facilitate hybridization between probe affixed on the chip and the target solution. For effective agitation in the chamber, the sample is mixed after filling a target solution up to a cover of the chamber so that the hybridization chamber is seriously contaminated.

FIGS. 4A and 4B are views of a conventional automatic hybridization system developed by Memorec Co. Referring to FIGS. 4A and 4B, after the sample is injected, hybridization, washing, and drying are automated. The hybridization system includes a diaphragm pump used to attain active circulation. In this case, however, a large amount of the sample, up to 220 μl, is needed because the sample must be circulated.

FIGS. 5A and 5B are view of a MAUI hybridization system obtained from Biomicro Co. Referring to FIGS. 5A and 5B, four chips can be tested in the same conditions. In this case, however, after attaching a patch or a gasket onto the chip and injecting the sample, washing and drying must be performed separately.

FIGS. 6A and 6B are views of a hybridization system obtained from Genomic Solution Co. disclosed in U.S. Pat. No. 6,432,696. Referring to FIGS. 6A and 6B, the flow and temperature of a fluid in a plurality of chips are controlled. In this case, however, the hybridization system does not include an agitation device to diffuse the sample.

As a result of research conducted to solve these problems occurring in the conventional hybridization systems, the inventors of the present invention have found that an automatic hybridization system can be implemented by controlling a pump and valves in a closed system and completed the present invention.

SUMMARY OF THE INVENTION

The present invention provides a hybridization system in which a pump and valves are controlled in a closed system.

The present invention also provides a hybridization system including a sealing pad integrated with a hybridization chamber.

The present invention also provides a hybridization system in which sample loading, agitation, washing, and drying are performed through a single channel.

According to an aspect of the present invention, there is provided a hybridization system for hybridizing a biochip including: a chamber device including at least a hybridization chamber including a support for a biochip and a first cover having a sample inlet; an agitation device including: two air channels connected to ends of the hybridization chamber; two valves disposed in the air channels; an integrated air channel to which the two air channels are connected; and an air pump disposed in the integrated air channel; and a washing and drying device including: a flow channel connected to one of the two air channels through a branched valve; a flow pump disposed in the flow channel; and a buffer inlet disposed opposite the flow channel.

A biomolecule to be affixed on a support to form a biochip may be selected from the group consisting of DNA, RNA, PNA (Peptide Nucleic Acid), LNA (Locked Nucleic Acid), peptide, and protein, but is not limited thereto. The support may be a solid support, such as glass, silicon, and plastic. The biochip can be obtained from other companies, if needed. The biochip may be placed on a biochip support after a cover of the hybridization system according to the present invention is opened.

An edge of the cover is connected to the support by a hinge such that the hybridization chamber can be opened or closed by the movement of other edge of the cover.

The hybridization system may further comprise a second cover including a cap which covers the sample inlet of the first cover.

An edge of the second cover may be connected to the first cover by the hinge such that the sample inlet is opened or closed by the movement of the other edge of the second cover.

The hybridization system may further include an air vent formed in the side surface of an upper portion of the sample inlet contacting the cap or in the side surface of a lower portion of the cap contacting the sample inlet.

The hybridization system may further include a sealing element that is integrated with a lower surface of the cover and surrounds the hybridization chamber.

The sealing element may include a protruding portion formed inside the hybridization chamber and a recessed portion formed outside the hybridization chamber.

The hybridization system may include a heater disposed below the hybridization chamber.

The hybridization system may be heated or cooled using a Peltier device.

The air channels connected to ends of the hybridization chamber may be connected to side walls of the sample inlet.

The air channel or the flow channel may have a circular cross section and may be formed by overlapping upper and lower substrates comprising grooves with a half-circular cross section The hybridization system may further include a sealing element that is integrated with the upper substrate or the lower substrate and surrounds the grooves of the upper substrate or the lower substrate.

The sealing element of the air channel or the flow channel may include a protruding portion formed inside the air channel or the flow channel and a recessed portion formed outside the air channel or the flow channel.

A solution contained in the hybridization chamber may be agitated by repeating an operation, which comprises: pumping air to the air pump when one of the valves is opened and the other valve is closed; pumping air from the air pump when the opened valve is closed and the closed valve is opened; pumping air to the air pump when the opening and closing of the valves are not changed; and pumping air from the air pump when the closed valve is opened and the opened valve is closed.

In this case, the pushing of the air pump of the agitation device indicates pushing air by using the air pump, not elevating of the air pump itself. Also, the pulling of the air pump of the agitation device indicates pulling air by using the air pump, not descending of the air pump itself.

The valves of the agitation device may be branched valves to control the supply of air to a plurality of hybridization chambers.

The branched valve refers to a valve connected to a plurality of channels. In this case, each channel can be independently opened or closed.

The valve may be a solenoid valve with a small amount of a death volume, but is not limited thereto.

The integrated air channel may be disposed in the air pump. In this case, two air channels exist in the single air pump.

Any pump that can increase or decrease the pressure of the air in the air channel by using electric signals can be used in the present invention. However, the use of a stepping motor-type micro pump in which the volume can be controlled in units of micrometers is preferable.

The flow channel of the washing/drying device may be connected to the air channel of the agitation device through the branched valve and the air channel is connected to a side wall of a sample inlet.

The hybridization system may further comprise an air line for drying connected to the flow channel of the washing/drying device through branched valve.

The hybridization system may be supplied with $N_2$ through the air line.

The flow pump may be a solenoid operated micro pump. However, any pump that can cause the flow of a fluid in first and second the air channels by using electric signals can also be used.

The hybridization system may further include a branched valve which controls the supply of a plurality of buffers and is connected to a plurality of buffer inlets disposed opposite the flow channel of the washing/drying device.

The hybridization system may further include: a computer CPU, which automatically controls the opening and closing of the valves, the operation of the pump, and the temperature of a heater; and a monitor displaying system operations.

According to another embodiment of the present invention, there is provided an integrated sealing element integrated with a surface of one of an upper substrate and a lower substrate and surrounding a space formed by overlapping the upper substrate and the lower substrate, the sealing element comprising: a protruding portion formed inside the space; and a recessed portion formed outside the space.

The space may be a chamber or a channel that is commonly used for a lap-on-a-chip, MEMS, or the like. However, any space required to from a space by overlapping the upper and lower substrates can also be used.

The integrated sealing element may be composed of a flexible polymer that can be transformed when being pressed, preferably silicon.

The protruding portion may be inclined toward the inside of the space. When the upper substrate and the lower substrate overlap, the transformation of the protruding portion is absorbed by the recessed portion adjacent to the protruding portion.

According to the present invention, only one of the upper substrate and the lower substrate has the protruding portion and the recessed portion. On the other hand, conventionally, each of the upper substrate and the lower substrate has the recessed portion, thus resulting in the requirement of a rubber O-ring. Therefore, according to the present invention, the manufacturing process for the micro flow channel or the chamber can be simplified, and the contamination of the micro flow channel and the chamber can be prevented. Further, the integration of the sealing element and the substrate contributes to ease of separation and cleaning.

The hybridization system is used to effectively diffuse a target solution to the chip. In order to effectively bind the target solution to the probe affixed on the chip, a micro pump alternatively pumps air in two directions and valves are controlled in a closed system.

The pump and the valve may be decreased to a few to several tens µm in size, thus being suitable for a micro array or a lab-on-a-chip, but is not limited thereto.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
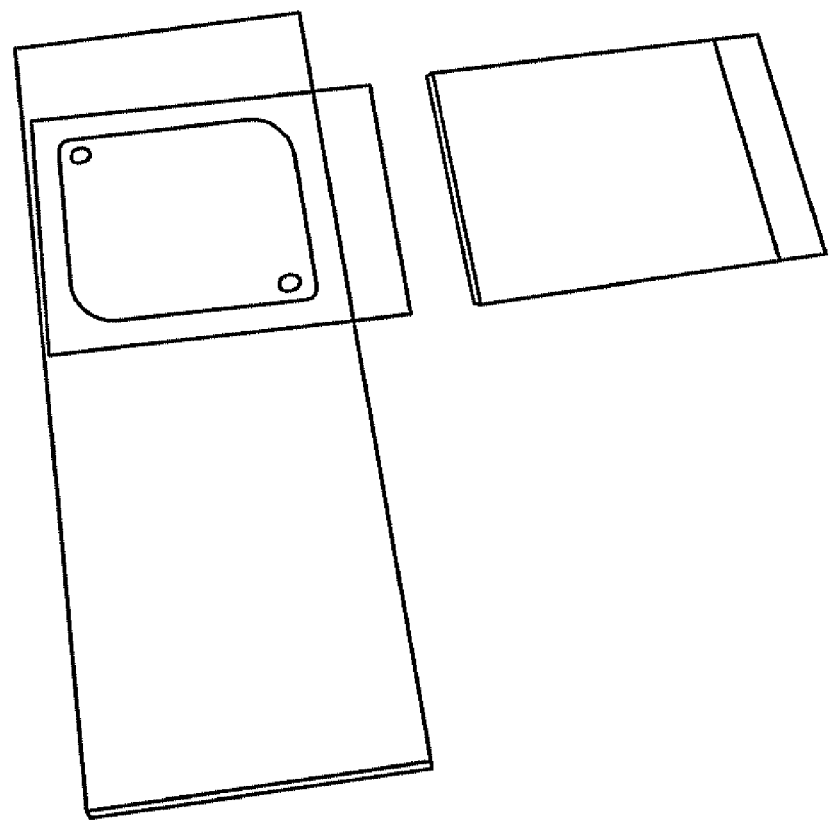
FIG. 1 illustrates a slide glass and a cover glass used for a conventional manual hybridization.
Figure 2A:
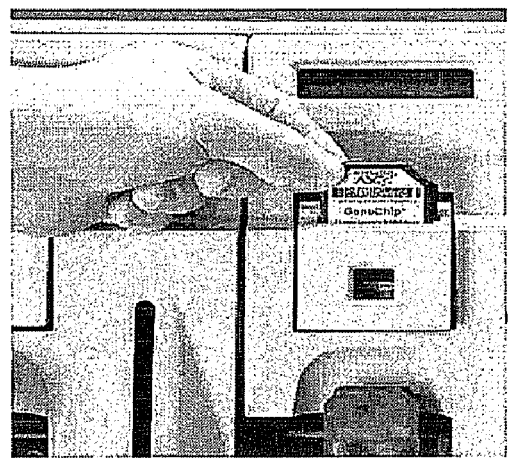
FIGS. 2A and 2B are views of a conventional hybridization system obtained from Affymetrix Co.
Figure 2B:
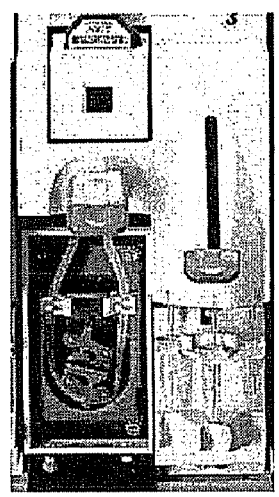
Figure 3A:
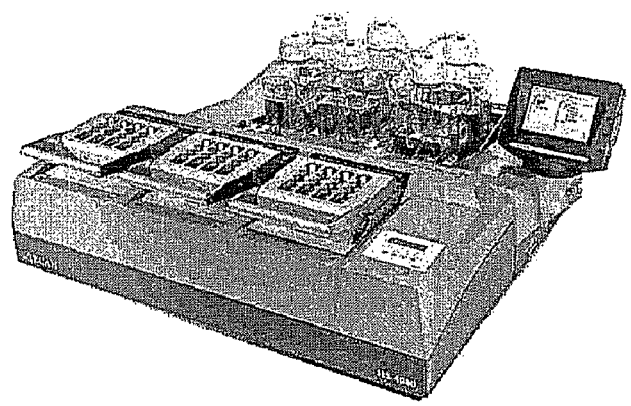
FIGS. 3A and 3B are views of a conventional hybridization system obtained from Tecan Co.
Figure 3B:
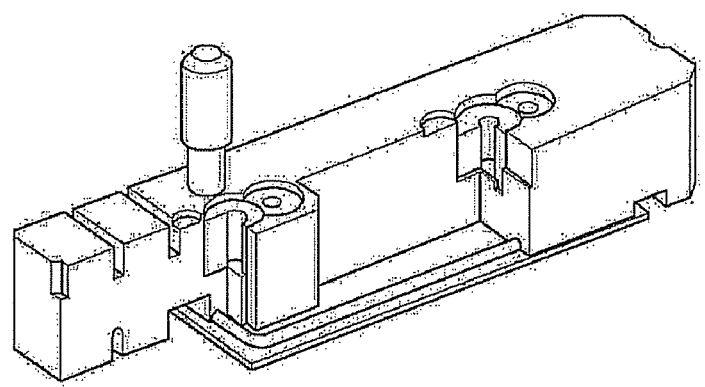
Figure 4A:
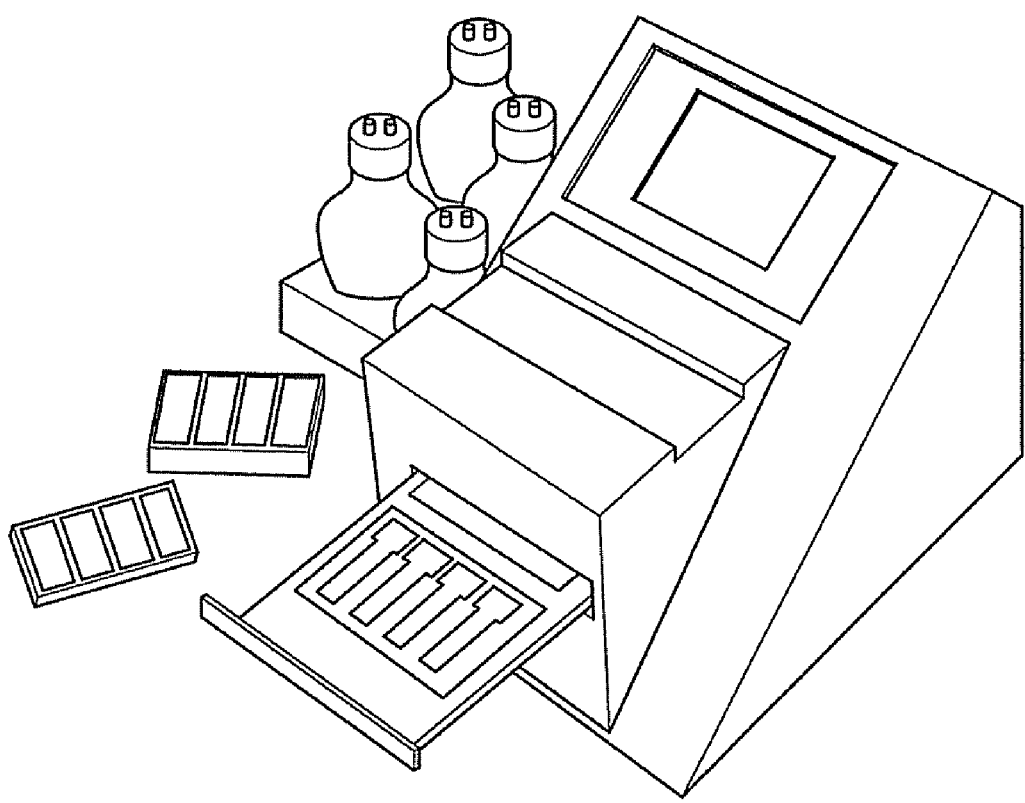
FIGS. 4A and 4B are views of a conventional A-Hyb hybridization system using an active circulation obtained from Memorec Co.
Figure 4B:
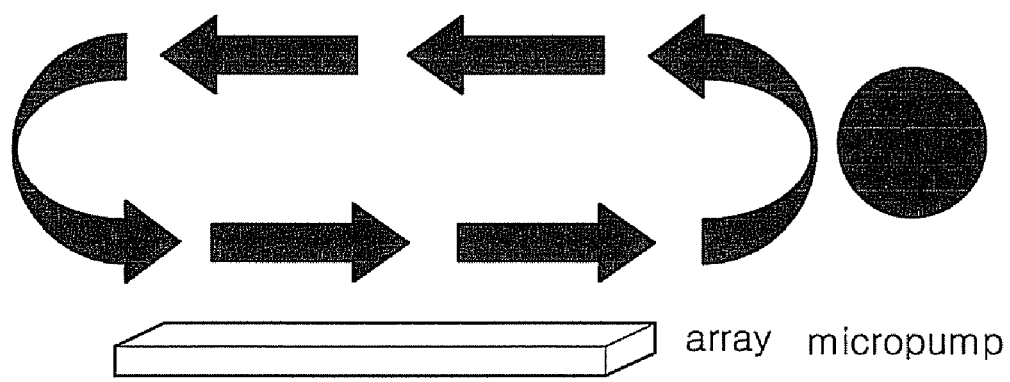
Figure 5A:
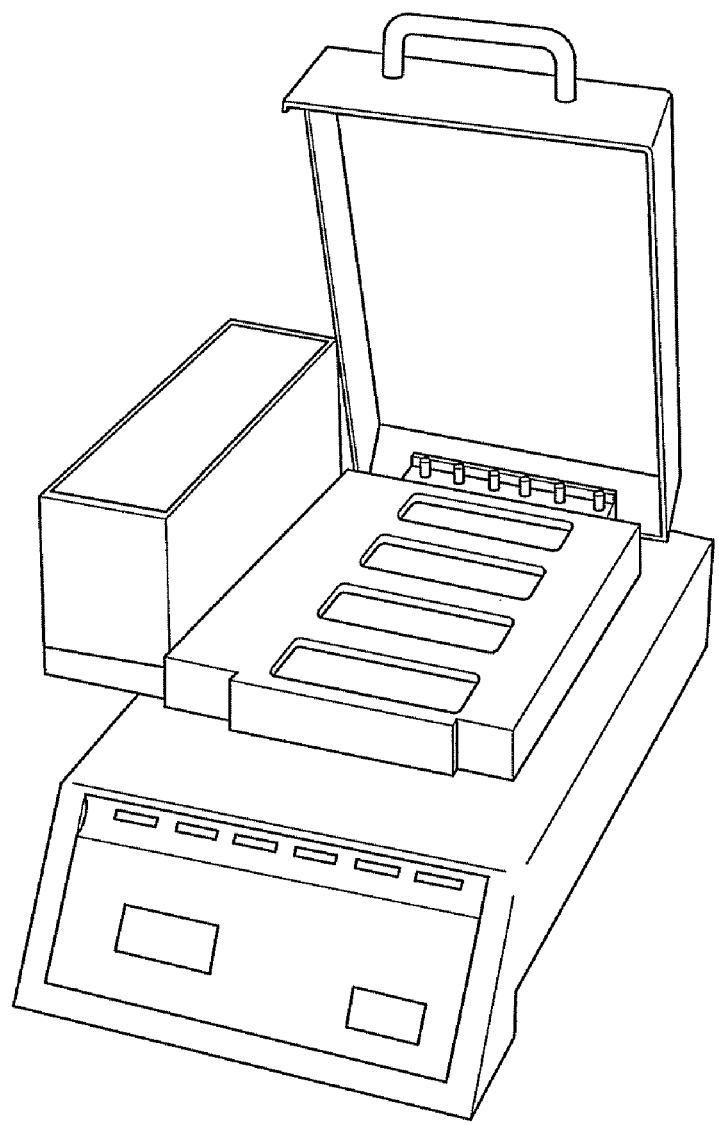
FIGS. 5A and 5B are views of a conventional MAUI hybridization system obtained from BioMicro Co.
Figure 5B:
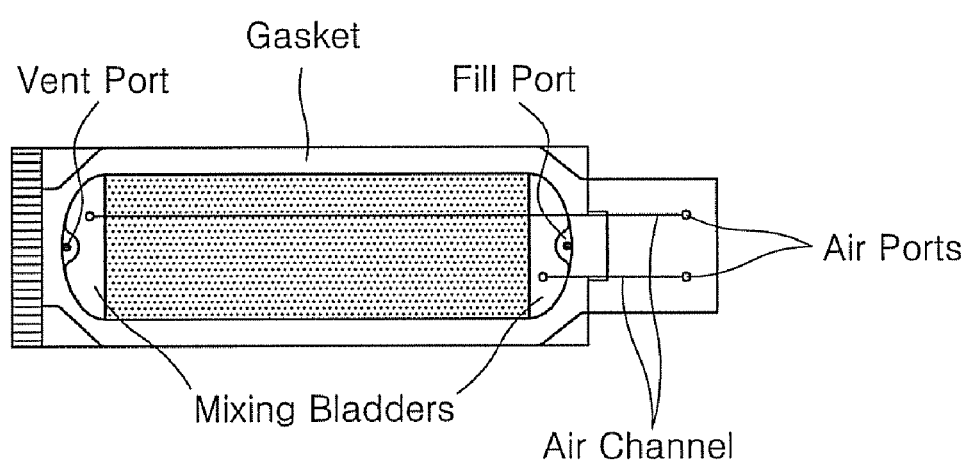
Figure 6A:
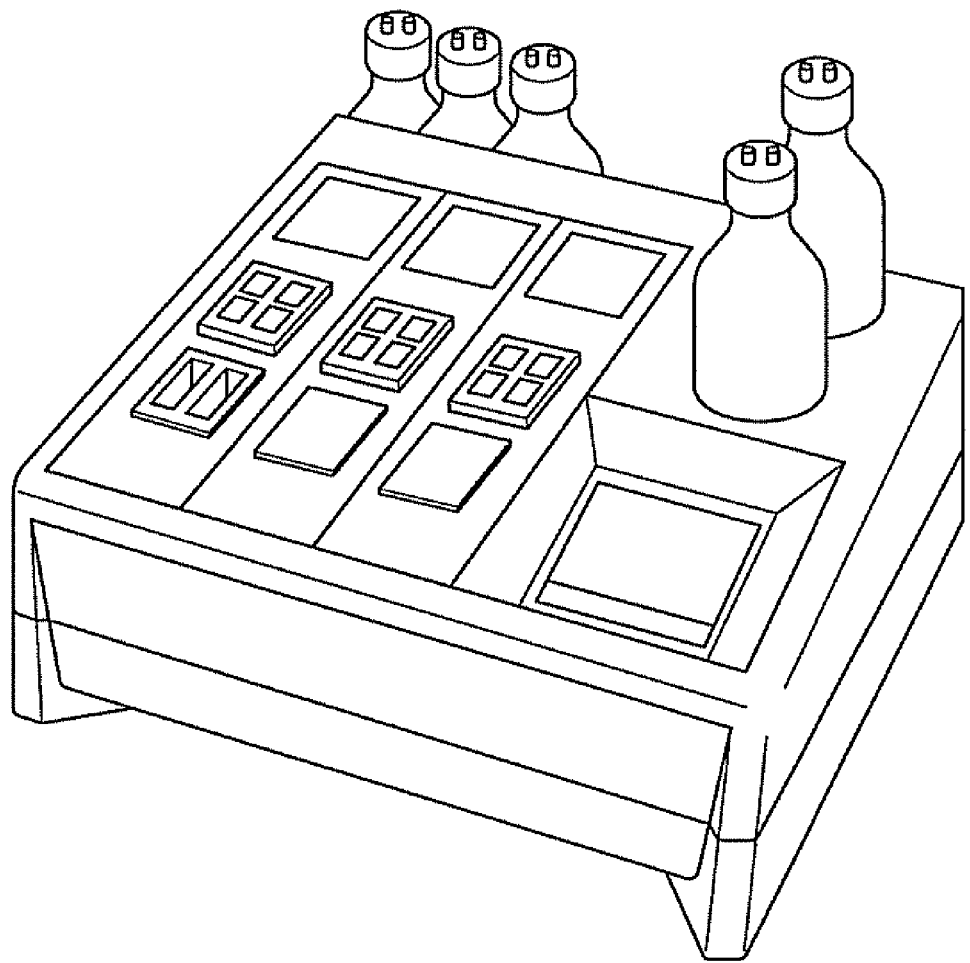
FIGS. 6A and 6B are views of a conventional hybridization system obtained from Genomic solution Co.
Figure 6B:
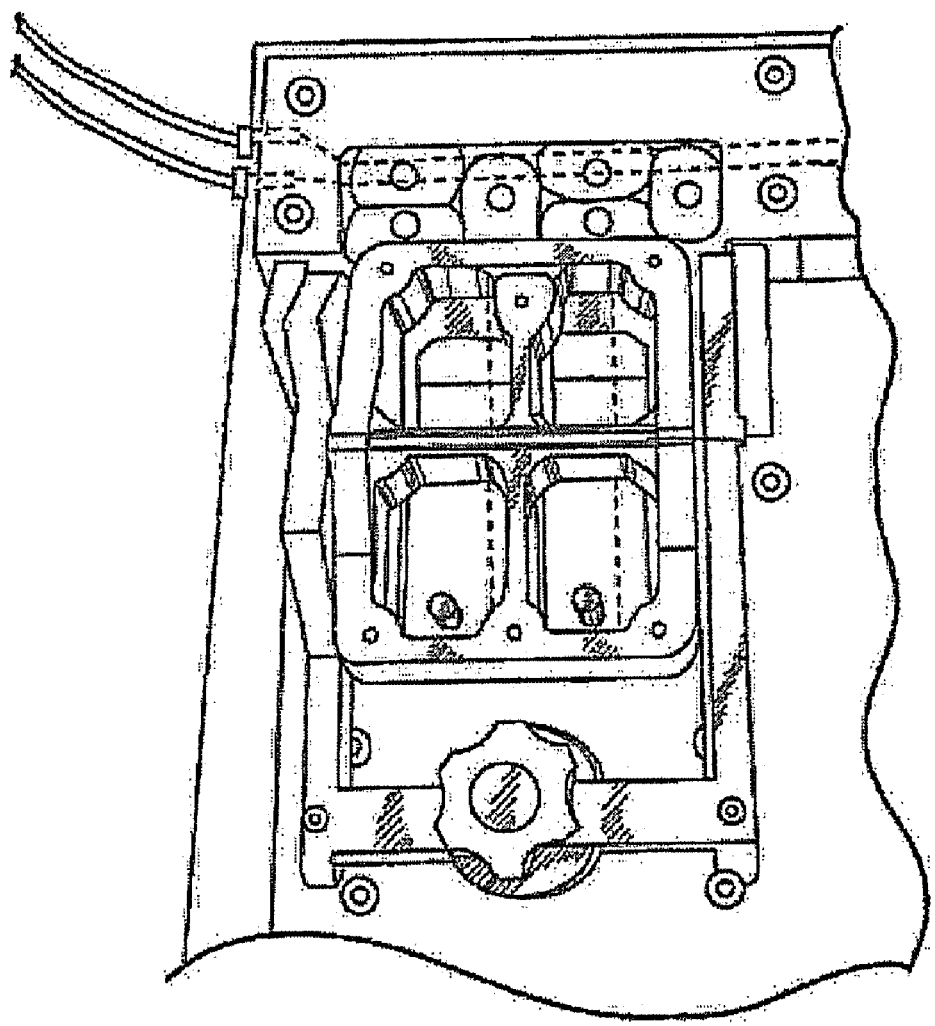
Figure 7:
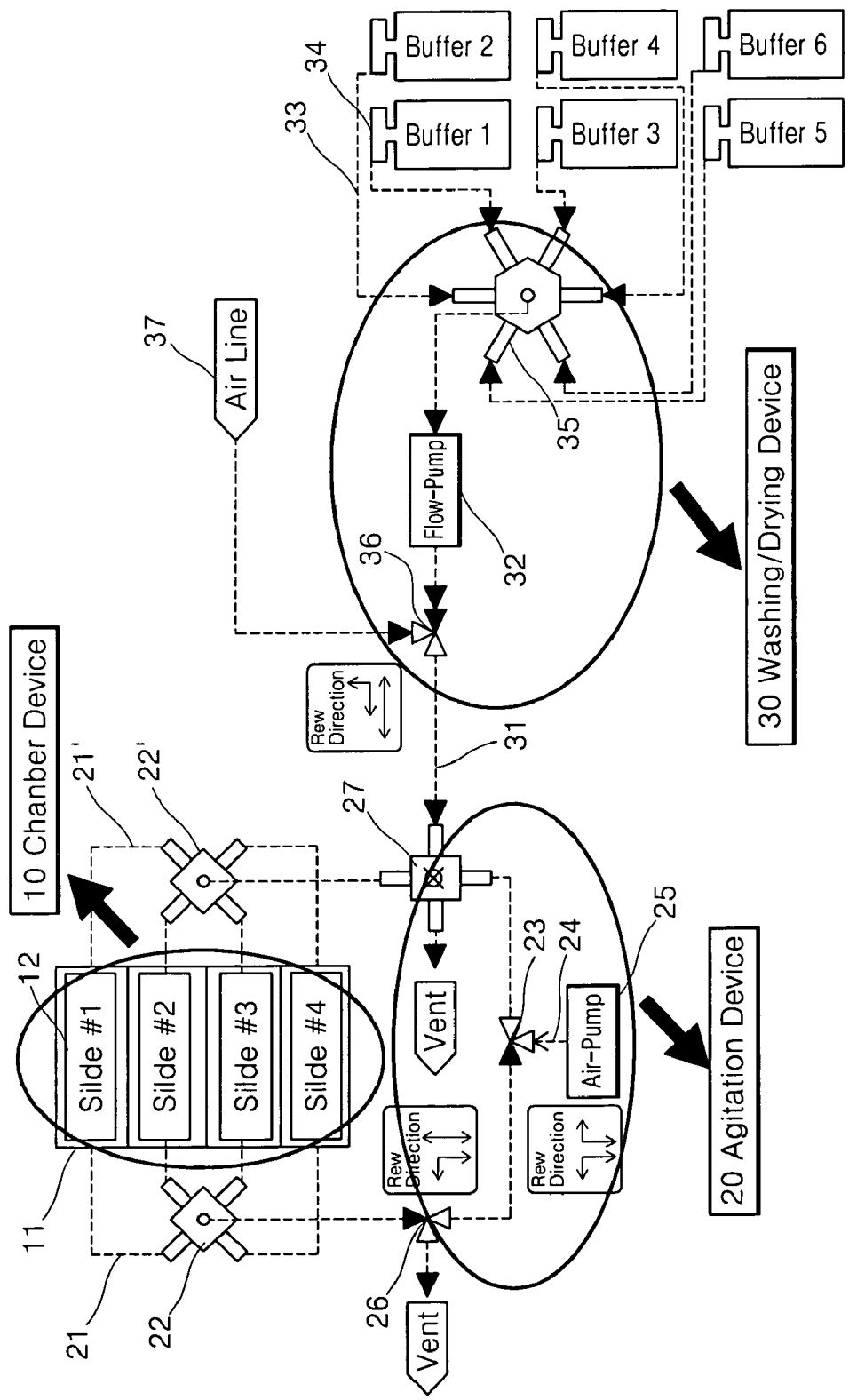
FIG. 7 is a schematic diagram of a hybridization system according to an embodiment of the present invention.

FIG. 7 is a schematic diagram of a hybridization system according to an embodiment of the present invention. Referring to FIG. 7, the hybridization system includes a chamber device 10, an agitation device 20, and a washing/drying device 30. The chamber device 10 includes at least one hybridization chamber 11 which includes a support for a biochip 12 and a cover having a sample inlet. The agitation device 20 includes air channels 21 and 21' connected to ends of the hybridization chamber 11, valves 22 and 22' disposed in the air channels 21 and 21', an integrated air channel 24 to which the air channels 21 and 21' are connected, and an air pump 25 disposed in the integrated air channel 24. The washing/drying device 30 includes a flow channel 31 connected to the air channel 21' through a first branched valve 27, a flow pump 32 connected to the flow channel 31, and a buffer inlet 33 disposed opposite the flow channel 31.

In FIG. 7, the chamber device 10 includes four hybridization chambers 11. Slides #1 to #4 act as biochips and are disposed on supports of the hybridization chambers 11, respectively. The hybridization chamber 11 is formed by pressing the cover disposed over a support. The chamber may have a rectangular form corresponding to the shape of the biochip, and is preferably streamlined such that uniform pressure can be applied to the hybridization chamber 11 by air injected through the air channels 21 and 21'. The sample may be manually loaded through the sample inlet formed in the cover by using a micropipette. However, the sample can be loaded using an automatic sample inlet device. A target molecule contained in the loaded sample is hybridized with a probe affixed on the biochip in the hybridization chamber 11.

The valves 22 and 22' disposed in the air channels 21 and 21' of the agitation device 20 may be branched valves to control the supply of air to the hybridization chambers 11. In the present embodiment, a 4 way agitating valve is used as the branched valve to provide air to the slides #1 to #4. The sample contained in the hybridization chamber 11 can be diffused by pumping air from and to the air pump 25 when the valves 22 and 22' are alternately opened and closed. In detail, the sample contained in the hybridization chamber 11 is agitated by repeating the following operations: pumping air from the air pump 25 when the valve 22 is opened and the valve 22' is closed; pumping air to the air pump 25 when the valve 22 is closed and the valve 22' is opened; pumping air from the air pump 25 when the valve 22 is closed and the valve 22' is opened; and pumping air to the air pump 25 when the valve 22 is opened and the valve 22' is closed. The solution contained in the hybridization chamber 11 can be mixed by repeating these operations. A valve 23 adjacent to the air pump 25 is a 3 way valve and acts as a connecting unit that sends a predetermined amount of the delivery pressure generated from the air pump 25 to air channels 21 and 21', and a valve 26 vents the pressures of the hybridization chamber 11 and air channels 21 and 21' to the outside.

The flow channel 31 of the washing/drying device 30 is connected to the air channel 21' through the first branched valve 27. In the present embodiment, the first branched valve 27 is a 4 way agitating valve. In detail, the first branched valve 27 has four branches respectively connected to a channel connected to the hybridization chamber 11, a channel connected to the air pump 24, the flow channel 31, and a vent. Therefore, the flow channel 31 of the washing/drying device 30 is connected to the hybridization chamber 11 through the air channel 21'. In this case, agitating air, a washing buffer, and drying air can pass through a single channel, the air channel 21.

An air line 37 supplying drying air can be directly connected to the first branched valve 27, or indirectly connected to the first branched valve 27 through a second branched valve 36 disposed in the flow channel 31 of the washing/drying device 30. The second branched valve 36 is a 3 way valve having three branches respectively connected to a flow channel connected to the hybridization chamber 11, a flow channel connected to the buffer, and a channel connected to the air line 37. $N_2$ gas may be supplied through the air line 37.

On the side of the washing/drying device 30 opposite to the flow channel 31, the buffer inlet 33 is connected to a buffer container 34. The buffer container 34 may be disposed inside or outside the hybridization system. When the buffer container 34 is disposed outside the hybridization system, the buffer inlet 33 is connected to the outside through a buffer line inlet formed in the hybridization system. Preferably, a third branched valve 35 may be further disposed between the flow channel 31 and the buffer inlet 33. The third branched valve 35 is connected to a plurality of buffer inlets 33 and controls the supply of a plurality of buffers. The third branched valve 35 may be a 6 way agitating valve to receive the buffers from the six buffer containers 33.

Figure 8A:
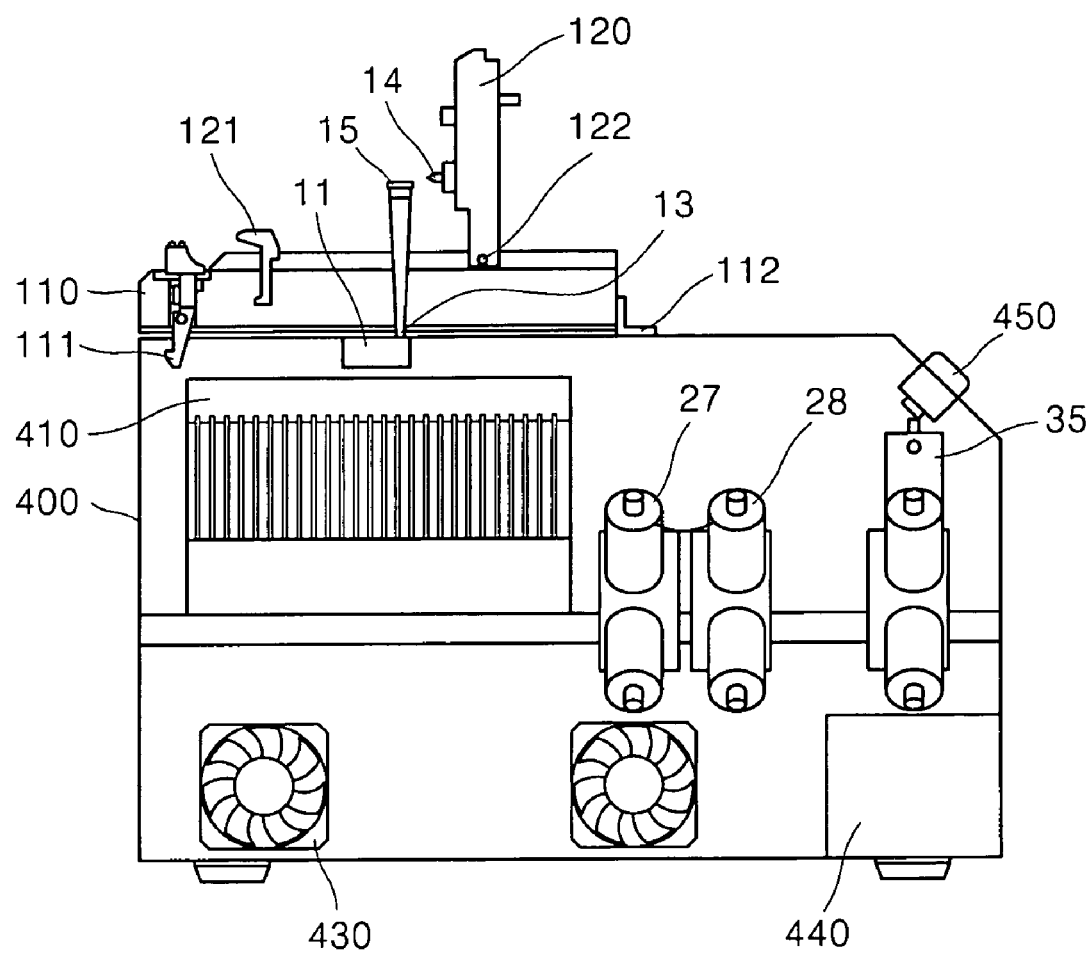
FIG. 8A is a sectional view of a hybridization system according to an embodiment of the present invention.

FIG. 8A is a sectional perspective view of a hybridization system according to an embodiment of the present invention. Referring to FIG. 8A, a first cover 110 connected to a main body 400 by a hinge 112 is closed by a hook 111. A second cover 120 connected to the first cover 110 by a hinge 122 is released from a hook 121. The sample is injected into the hybridization chamber 11 through a sample inlet 13 using a micro pipette 15. The second cover 120 includes a cap 14 that covers the sample inlet 13 of the first cover 110. A heater 410 is disposed below the hybridization chamber 11. The main body 400 includes an agitation device (not shown); a washing/drying device including the first branched valve 27, the second branched valve 36, and the third branched valve 35; a buffer line inlet 450 connected to a buffer container, which is disposed outside the system; an air pan 430 removing heat generated inside the main body 400; and an air pump 440. In addition, an LCD monitor 420 displaying system operations is disposed on a slanted outer surface of the main body 400.

Figure 8B:
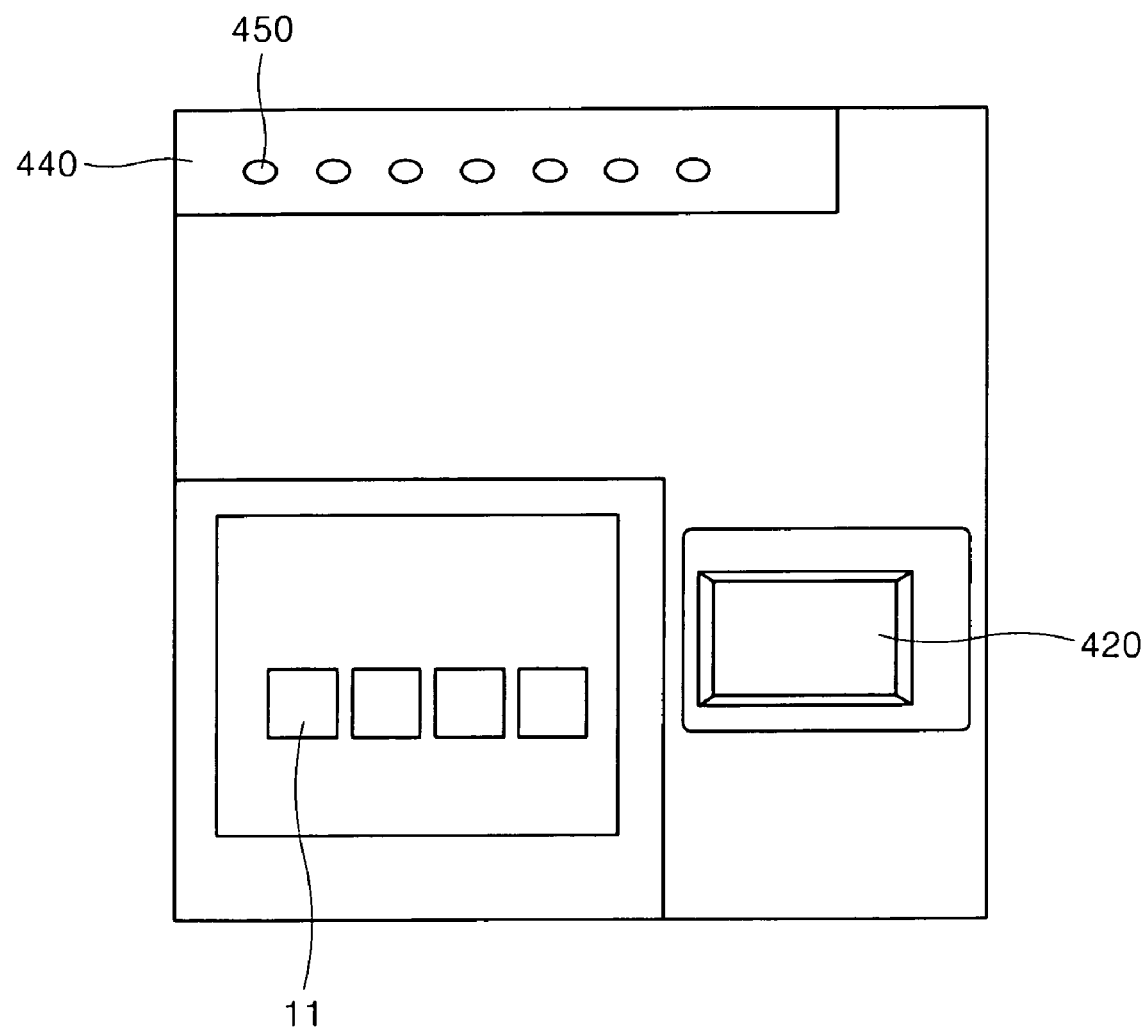
FIG. 8B is a plan view of the hybridization system shown in FIG. 8A.

FIG. 8B is a plan view of the hybridization system shown in FIG. 8A. Referring to FIG. 8B, a chamber device including four of the hybridization chambers 11 is disposed in a left lower portion of the hybridization system, the LCD monitor 420 displaying system operations is disposed in a right portion of the hybridization system, and the buffer line inlets 450 are disposed on outer surface of the hybridization system.

Figure 8C:
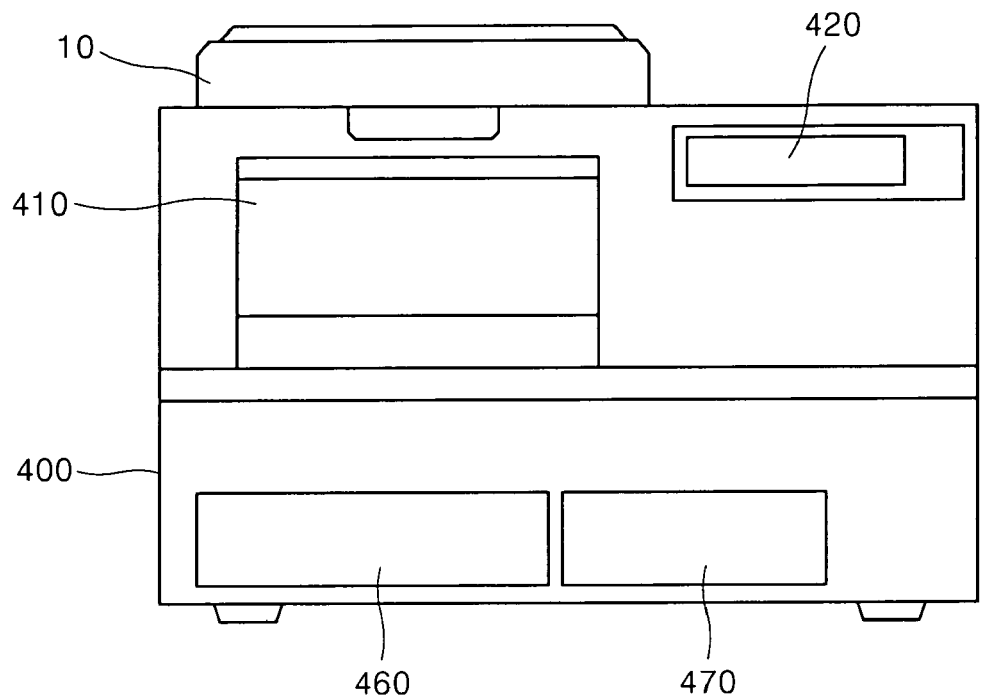
FIG. 8C is a front view of the hybridization system shown in FIG. 8A.

FIG. 8C is a front view of a hybridization system according to an embodiment of the present invention. Referring to FIG. 8C, the first cover 110 is disposed on the main body 400, a heater is disposed below a hybridization chamber, the LCD monitor 420 displaying system operations is disposed in a right upper portion of the hybridization system, a computer CPU 460 automatically controls a pump and the temperature of the heater 410 and is disposed in a lower portion of the main body 400, and a power supply unit 470, which supplies a power.

Figure 9:
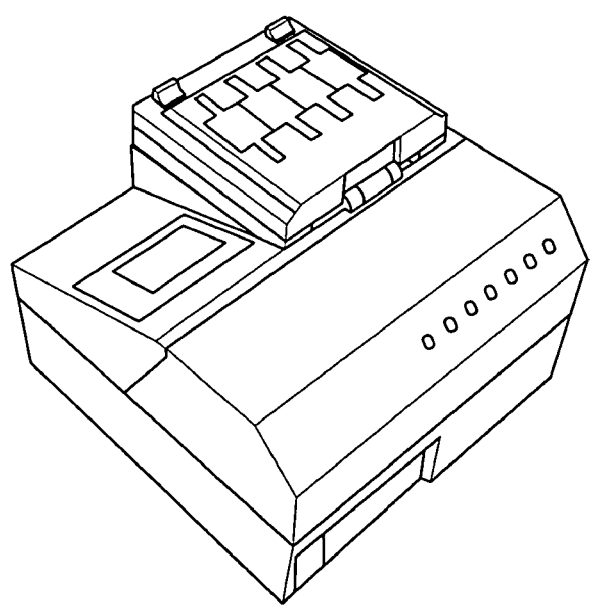
FIG. 9 is an image of the hybridization system shown in FIG. 8A.

FIG. 9 is a photograph of the hybridization system shown in FIG. 8A. The hybridization system may have a maximum size of 30×30×25 (unit:cm), and can be mass-produced for $7,500 or less. Further, the hybridization system can interface with PCs; the hybridization system can be connected to a plurality of HS devices; the hybridization system includes a controller and an LCD panel such that the hybridization system can independently operate; four test chips can be used at the same time; the hybridization system can operate at a temperature of 0 to 80° C.; the agitation for hybridization is performed using a pump; washing is performed using a fluid flow, which is generated using the pump; and air blowing is used for drying.

Figure 10A:
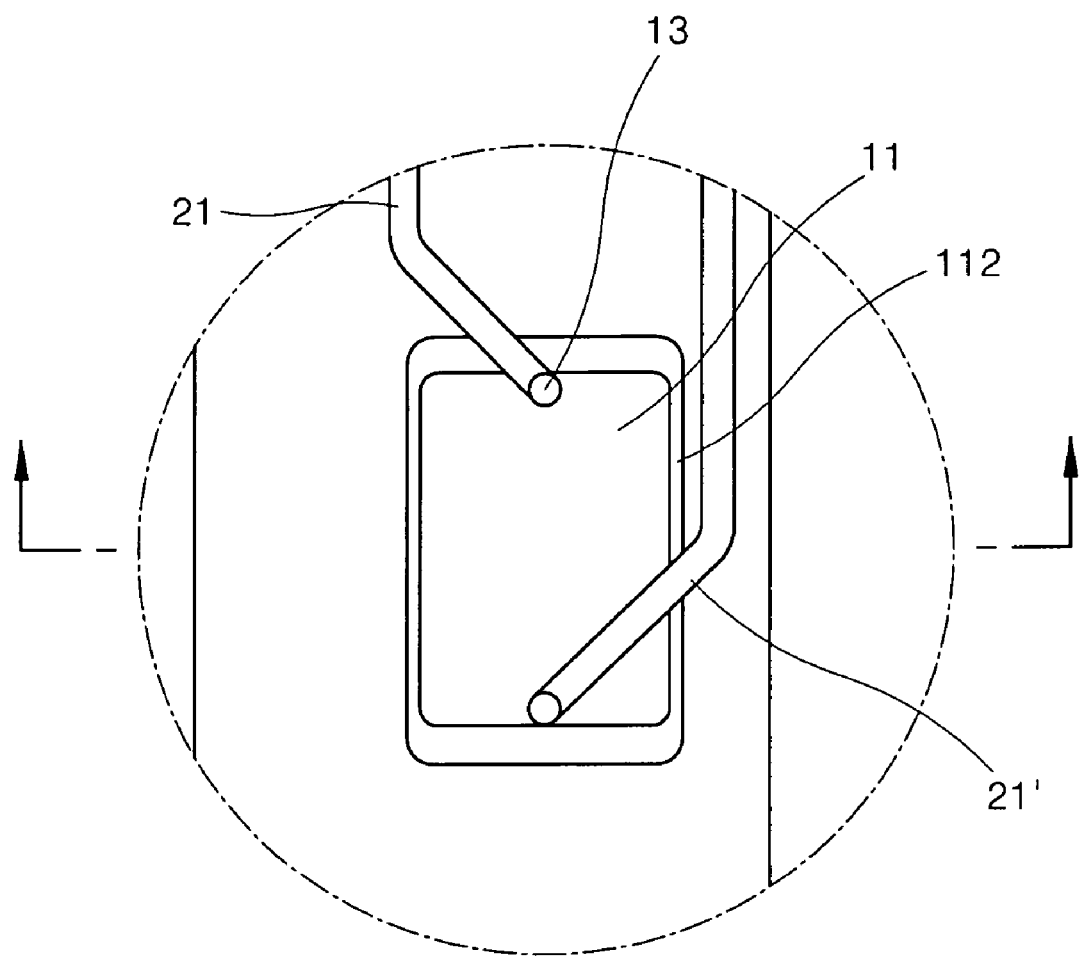
FIG. 10A is a horizontal sectional view of the hybridization system shown in FIG. 8A.
Figure 10B:
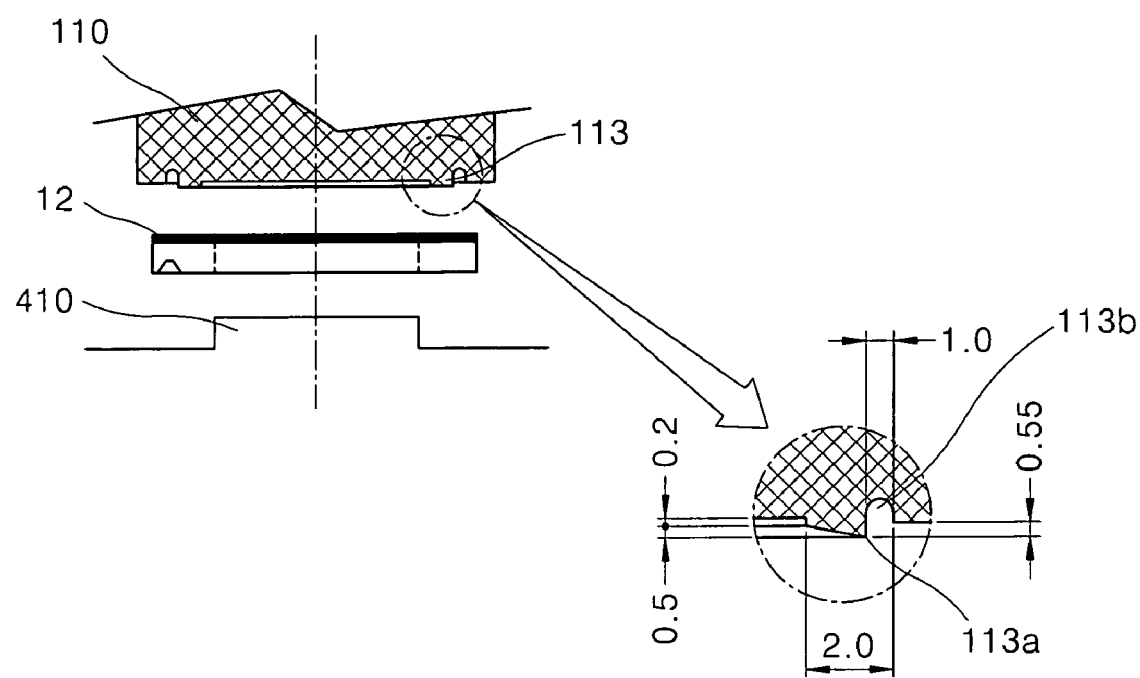
FIG. 10B is a sectional view taken along the bold line shown in FIG. 10A illustrating a sealing element.

FIG. 10A is a horizontal sectional view of the hybridization chamber 11 of the hybridization system shown in FIG. 8A. Referring to FIG. 10A, the hybridization chamber 11 is connected to the air channels 21 and 21' via the sample inlet 13 formed at ends of the hybridization chamber 11. The air channels 21 and 21' are arranged in the same direction toward a hinge, thereby allowing the opening and closing of a cover. FIG. 10B is a horizontal sectional view taken along the bold line shown in FIG. 10A illustrating a sealing element 113. Referring to FIG. 10B, the biochip 12 disposed on the supporter of the hybridization chamber 11 is covered by the first cover 110. The heater 410 is disposed below the hybridization chamber 11. The sealing element 113 is integrated with and is disposed in a lower surface of the first cover 110, along an edge of the hybridization chamber 11. The sealing element 113 of the hybridization chamber 11 includes a protruding portion 113a inside the hybridization chamber 11, and a recessed portion 113b outside the hybridization chamber 11. The sealing element 113 may be composed of any polymer that is flexible when pressed, preferably silicon.

Figure 11A:
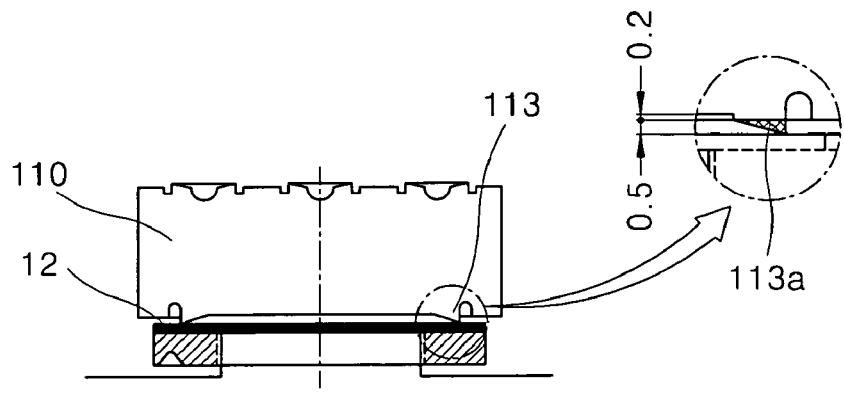
FIGS. 11A through 11C illustrate a method of operating the sealing element.
Figure 11B:
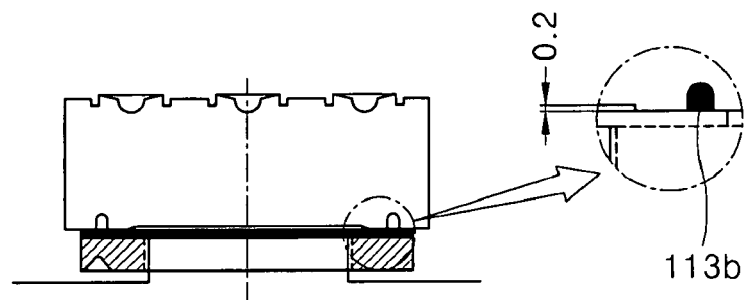
Figure 11C:
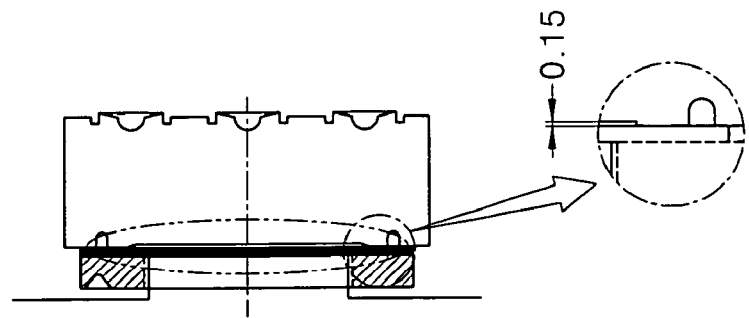

FIGS. 11A through 11C illustrate a method of operating the sealing element 113. Referring to FIG. 11, the biochip 12 of the hybridization chamber disposed on the support is covered by the first cover 110. Initially, the first cover 110 is not completely closed and the protruding portion 113a of the sealing element 113 is not transformed (FIG. 11A). At this time, the height of the hybridization chamber 11 is 0.7 mm, which is the sum of the own height of the hybridization chamber 11 of 0.2 mm, and the height of the protruding portion 113a of 0.5 mm. Next, the first cover 110 is completely closed and the protruding portion 113a is pressed, thus being transformed (FIG. 11B). The transformation of the protruding portion 113a is absorbed by the recessed portion 113b adjacent to the protruding portion 113a. At this time, the height of the hybridization chamber 11 is equal to the own height of the hybridization chamber 11, 0.2 mm. Then, the hybridization chamber 11 is pressed to a height of 0.15 mm, thus decreasing the amount of the sample (FIG. 11C).

Figure 12A:
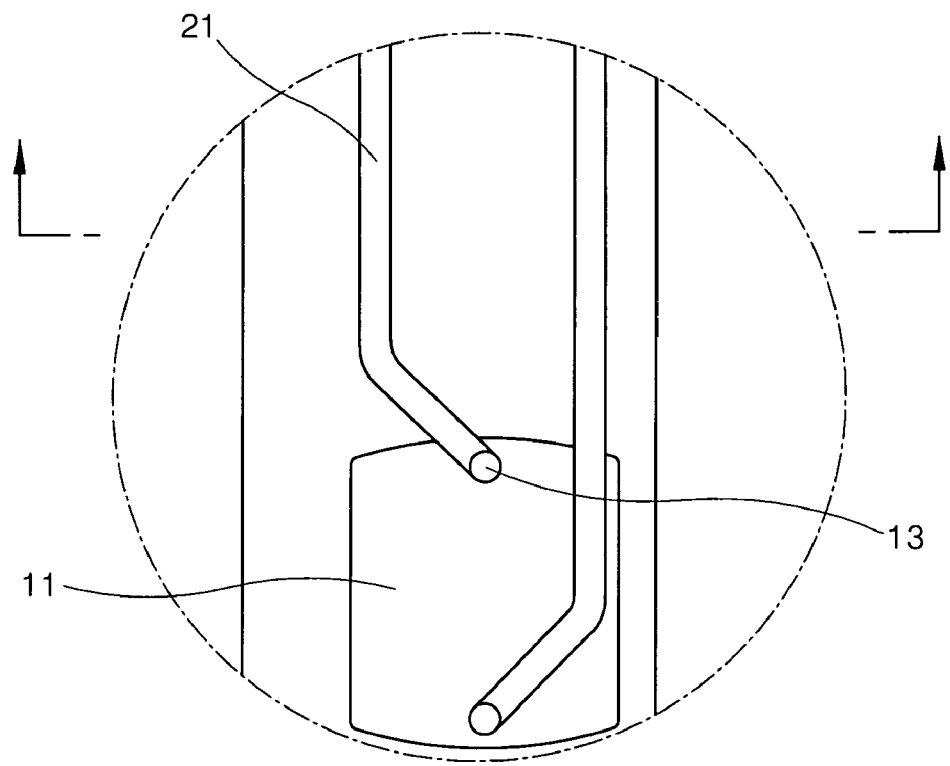
FIG. 12A is a horizontal sectional view of an air channel or a flow channel of the hybridization system shown in FIG. 8A.
Figure 12B:
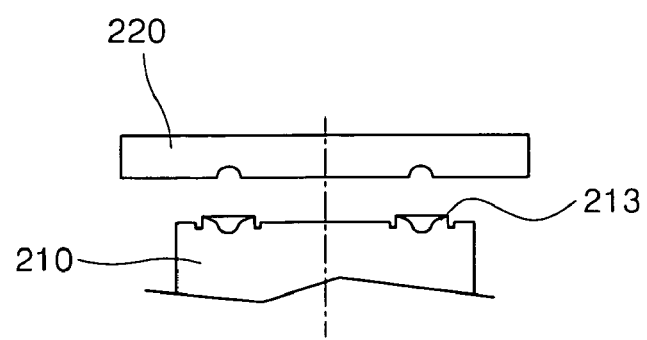
FIGS. 12B through 12D are sectional views taken along the bold line shown in FIG. 12A illustrating a sealing element.
Figure 12C:
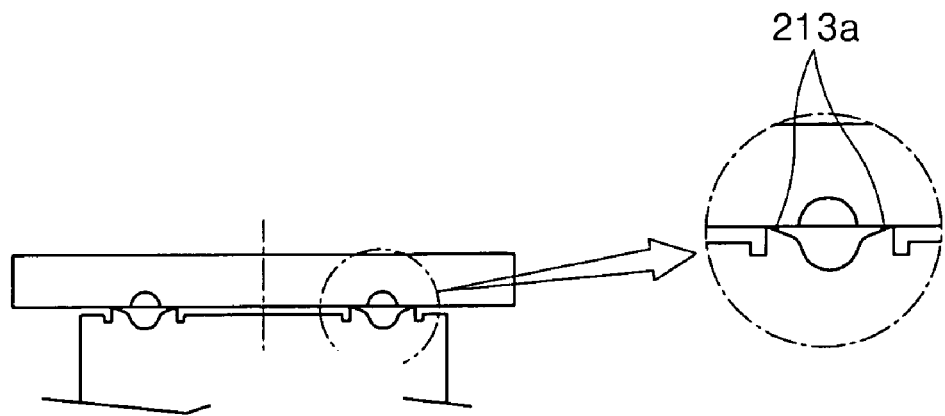
Figure 12D:
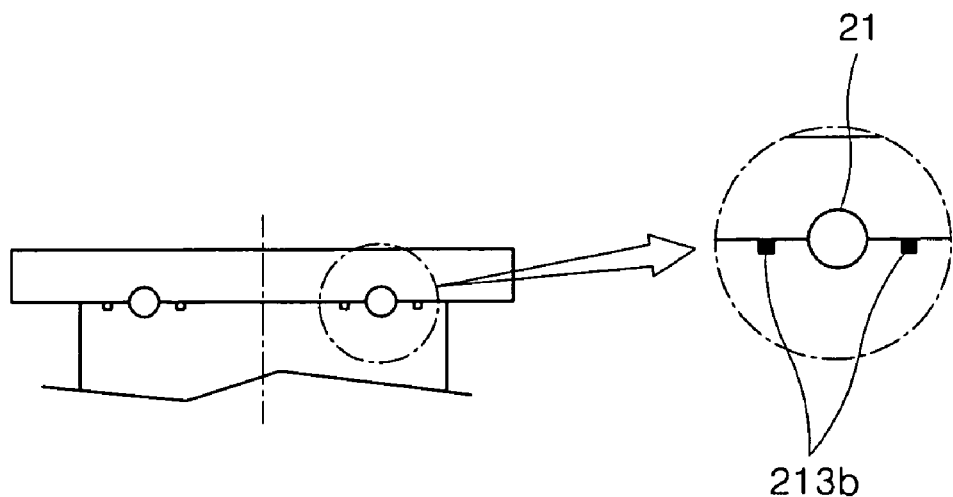

FIG. 12A is a horizontal sectional view of the air channels 21 and 21' of the hybridization system shown in FIG. 8A. Referring to FIG. 12A, the hybridization chamber 11 is connected to the air channels 21 and 21' via the sample inlet 13 formed at ends of the hybridization chamber 11. The air channels 21 and 21' are arranged in the same direction toward a hinge, thereby allowing the opening and closing of a cover. FIGS. 12B through 12D are sectional views taken along the bold line shown in FIG. 12A illustrating a sealing element 213. Referring to FIG. 12B, a channel or a flow channel with a circular cross section is formed by overlapping an upper substrate 220 and a lower substrate 210, which have grooves with semi-circular cross sections. A sealing element 213 integrated with the upper substrate 220 and the lower substrate 210 is formed outside the groove of the upper substrate 220 and the lower substrate 210. The sealing element of the channel or the flow channel includes a protruding portion 213a formed inside the channel or the flow channel and a recessed portion 213b formed outside the channel of the flow channel. The sealing element 213 may be composed of any polymer that is flexible when pressed, preferably silicon. Referring to FIG. 12C, the upper substrate 220 is not completely coupled to the lower substrate 220. Referring to FIG. 12D, the upper substrate 220 is completely coupled to the lower substrate 220 and the protruding portion 213a is pressed, thus being transformed. The transformation of the protruding portion 213a is absorbed to the recessed portion 213b adjacent to the protruding portion 213a. As a result, a channel 21 is formed.

Figure 13A:
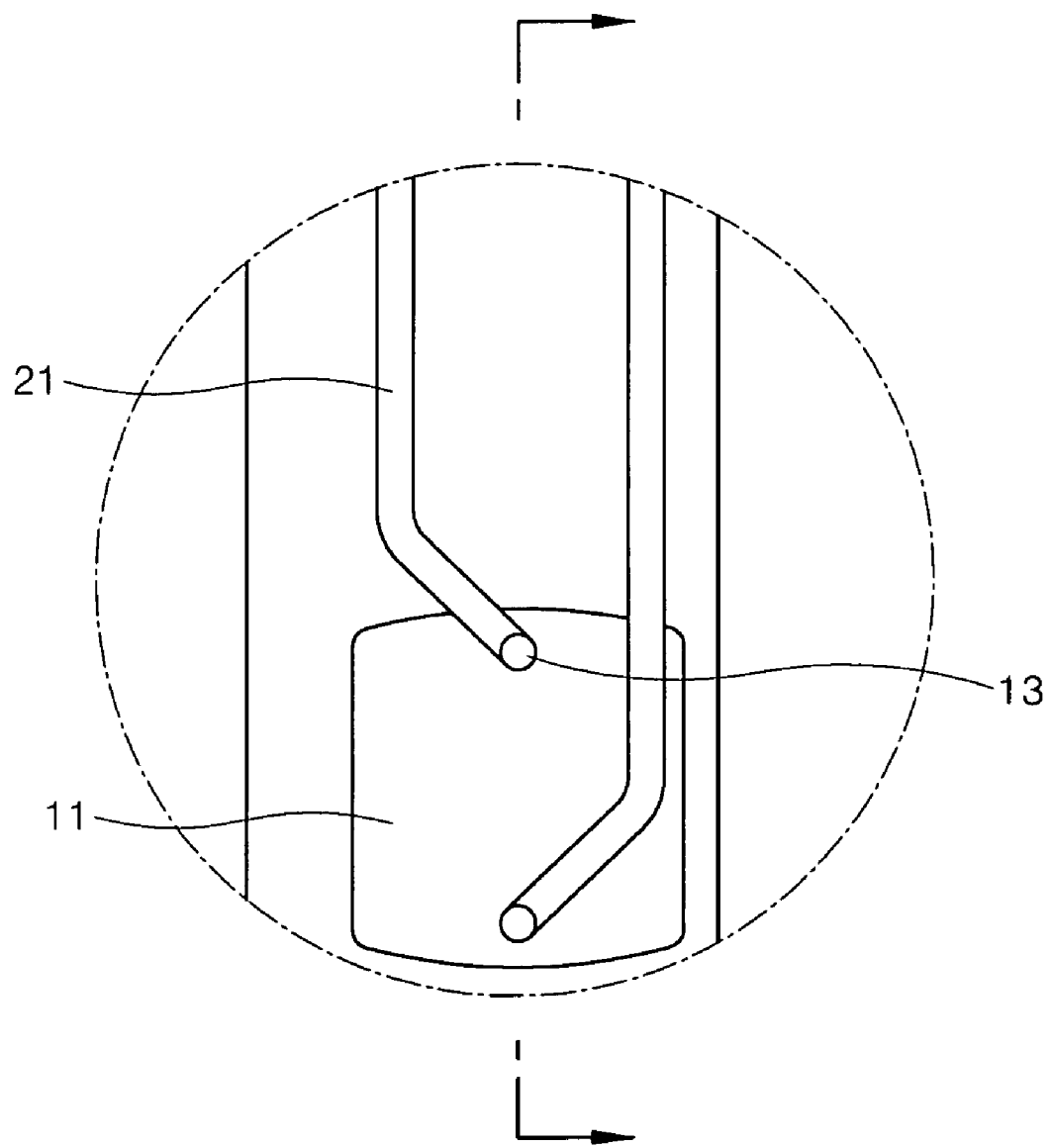
FIG. 13A is a horizontal sectional view of a sample inlet and an air channel of the hybridization system shown in FIG. 8A.
Figure 13B:
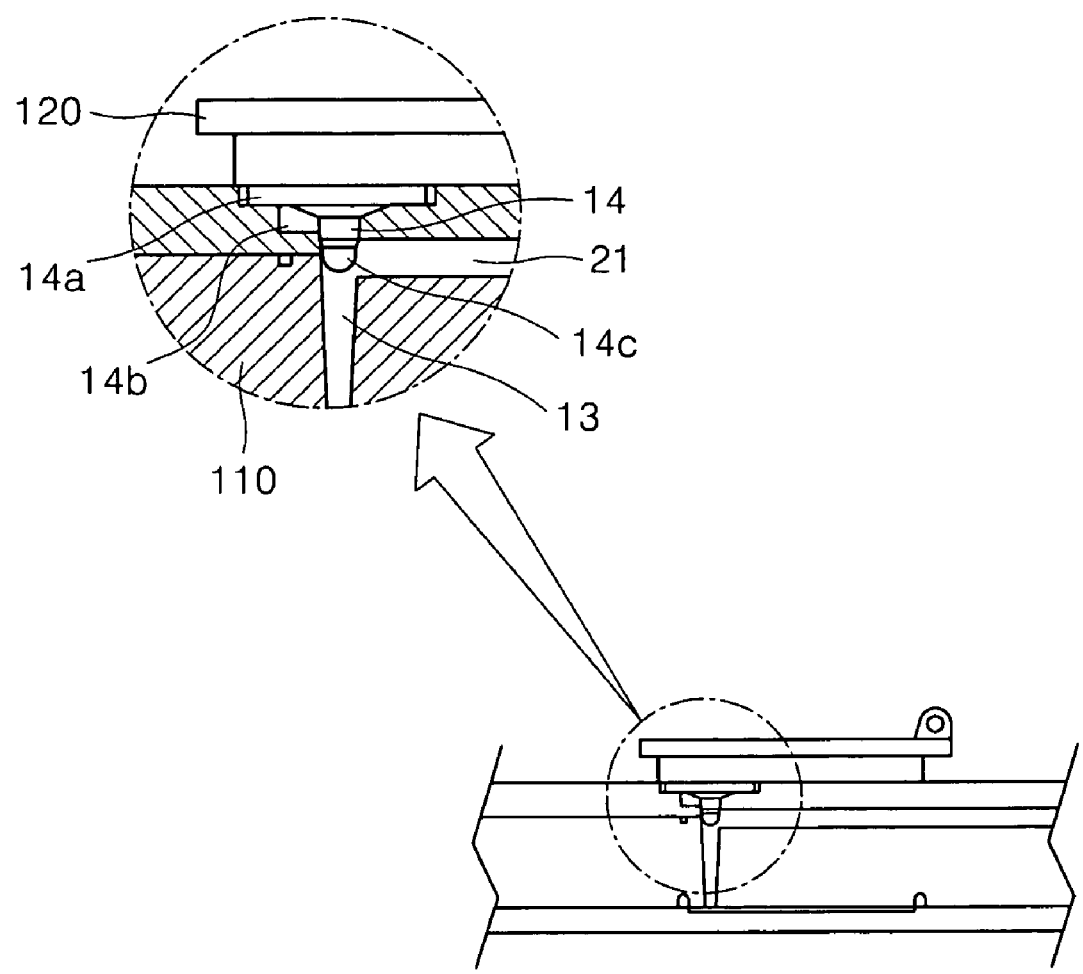
FIG. 13B is a sectional view taken along the bold line shown in FIG. 13A, and an enlarged sectional view illustrating a cover.

FIG. 13A is a horizontal sectional view of the sample inlet 13 and the air channels 21 and 21' of the hybridization system shown in FIG. 8A. Referring to FIG. 13A, the hybridization chamber 11 is connected to the air channels 21 and 21' via the sample inlet 13 formed at ends of the hybridization chamber 11. The air channels 21 and 21' are arranged in the same direction toward a hinge, thereby allowing the opening and closing of a cover. FIG. 13B is a sectional view taken along the bold line shown in FIG. 13A, and an enlarged view of the first cover 110 and the second cover 120. Referring to FIG. 13B, the sample inlet 13 is formed in the cover 110, and the sample inlet 13 is closed using the cap 14 formed in the second cover 120. The air channel 21 is connected to a side wall of the sample inlet 13, and ultimately to ends of the hybridization chamber 11. An air vent 14b is formed in a part of an upper portion of the sample inlet 13. The existence of the air vent 14b results in a decrease of air pressure in the sample inlet 13 when a lower surface 14a of the cap 14 contacts an upper surface of the first cover 110 and a cap top 14c is injected into the sample inlet 13. Therefore, the movement of the sample contained in the hybridization chamber 11 due to the air pressure can be prevented. A cap top 14c is separated from the side surface of the sample inlet 13. Therefore, a buffer remaining after washing can leak into the space formed between the cap top 14c and the side surface of the sample inlet 13 through capillary action. Therefore, contamination due to the residual buffer can be prevented. When the space is not formed, the residual buffer may leak into the hybridization chamber 11 readily when operation of drying, thus contaminating the hybridization chamber 11.

Figure 13C:
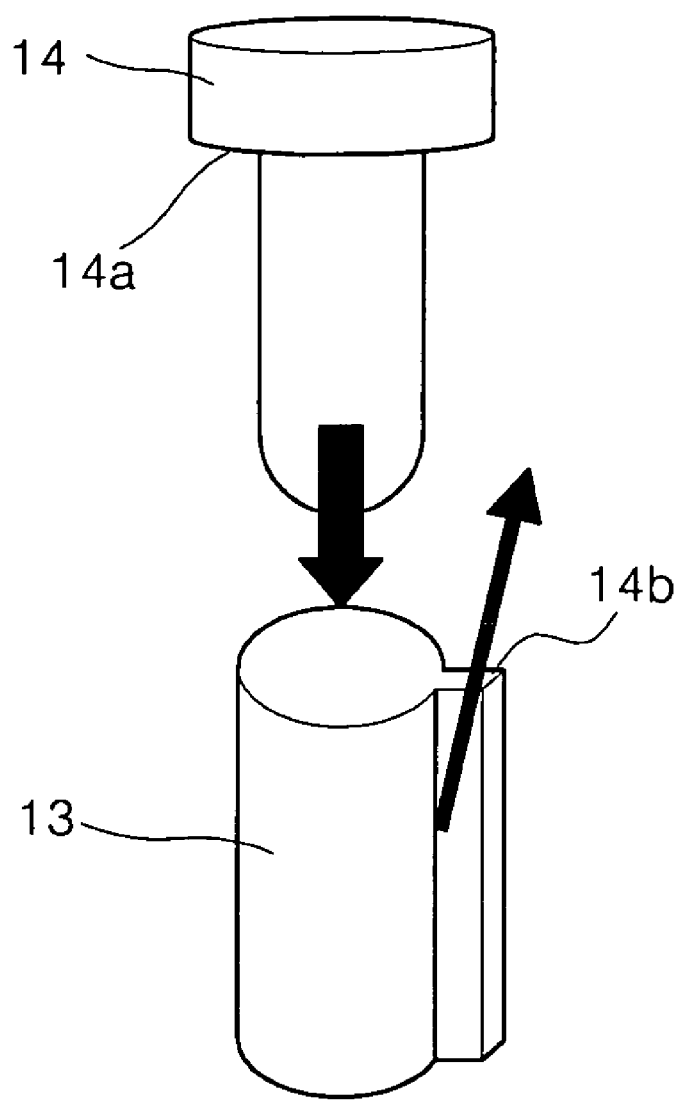
FIG. 13C is a view of a packing device of the hybridization system shown in FIG. 8A.

FIG. 13C is a view of a packing device of the hybridization system shown in FIG. 8A. Referring to FIG. 13C, the packing device includes the air vent 14b formed in the side surface of an upper portion of the sample inlet 13 contacting the cap 14. The air vent 14b is formed in a grooved shape with a predetermined depth from the upper surface of a side wall of the sample inlet 13. The air vent 14b allows for air pressure generated due to a volume of the cap 14 when the cap 14 is inserted into the sample inlet 13 to be released in an arrow direction (↑).

Figure 13D:
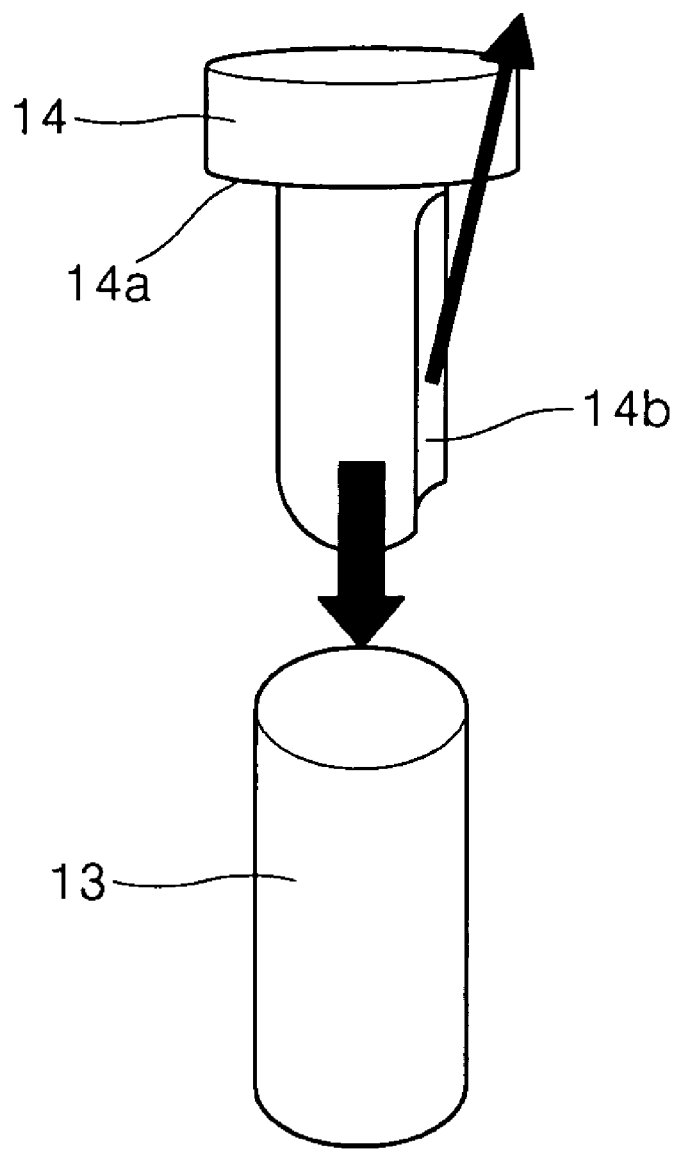
FIG. 13D is a view of a packing device of the hybridization system shown in FIG. 8A.

FIG. 13D is a view of the packing device of the hybridization system shown in FIG. 8A. Referring to FIG. 13D, an air vent 14b is formed in the side surface of a lower portion of a cap 14 contacting the sample inlet 13, which is formed in the upper cover of the chamber. The air vent 14b is a recessed portion with a predetermined length formed in the extended portion of the cap 14. The air vent 14b allows air pressure generated due to a volume of the cap 14 when the cap 14 is inserted to the sample inlet 13 to be released in an arrow direction(↑). The sample inlet 13 is sealed by closely contacting the lower surface 14a of an upper portion of the cap 14 with the sample inlet 13. The diameter of the upper portion of the cap 14 is greater than the diameter of the sample inlet 13.

Hereinafter, the present invention will be described in detail by explaining exemplary embodiments of the invention.

EXAMPLE

Application of Hybridization system according to the present invention

A MODY3 chip hybridized using a hybridization system hybridization method was compared with a MODY3 chip hybridized using a conventional cover slide patch method. The probes indicated in Table 1 were used.

First, the probes, which corresponds to a target nucleic acid MODY3, were affixed on a substrate, thus forming a microarray. In detail, a wild probe (WP) and a mutant probe (MP) were added to a solution mixture of polyethylenglycol (PEG), which has a molecular weight of 10,000, 0.025M (pH 10) of a sodium carbonate buffer, and formamide in a weight ratio of 1:1:2. The resulting solution was spotted on a silicon wafer using a bio-robot printer (Model No. PixSys 5500, obtained from Cartesian Technologies, Inc., CA, USA), and the silicon wafer was sit in a wet incubator at 37° C. for 4 hours. Then, the surrounding noise was controlled such that portions of the silicon wafer that were not spotted were subjected to an appropriate reaction, thereby providing a negative charge to the amine group adhered to the surface of the wafer. Therefore, adherence of the target nucleic acid to the silicon wafer could be prevented. The resulting silicon wafer was placed in a drying device. In the present example, the body or ends of the target nucleic acid (tgggttctgccctttgcgctgggatggt-gaagcttccagcc) was tagged with Cy3-dUTP as a fluorescent material. 187 nM of the target nucleic acid dissolved in 0.1% of a 6× SSPET solvent (Saline Sodium Phosphate EDTA Buffer containing 0.1% of Triton X-100), and the microarray reacted at 37° C. for 16 hours. Separately, 187 nM of the target nucleic acid dissolved in 0.1% of a 6× SSPET solvent (Saline Sodium Phosphate EDTA Buffer containing 0.1% of Triton X-100), and the microarray were hybridized using the hybridization system according to an embodiment of the present invention. Each of the chips was washed with 0.05% 6× SSPET for 5 minutes and 0.05% 3× SSPET for 5 minutes, dried at room temperature for 5 minutes, and then scanned by an Axon scanner (Model GenePix 4000B, Axon Instrument, Inc., CA, USA). The scanning data was analyzed using GenePix Pro 3.0 (obtained from Axon Instrument, Inc., CA, USA), thus obtaining ratio components and intensity components. The conditions for the processes are shown in Table 2.

TABLE 2

| | Hybridization time | Washing time | Drying time | Amount of sample used | Note |
| --- | --- | --- | --- | --- | --- |
| Traditional method | 4 hr | 10 min | less than 1 min | 60 ul | the other conditions were the same |
| Hybstation method | 30 min | 6 min | 30 sec | 45 ul | same |

TABLE 1

| WP | sequence | MP | Sequence |
| --- | --- | --- | --- |
| E02-01rwp | gacttgaccatcTTCgccacacg | E02-01rmp | gacttgaccatcTCCgccacacg |
| E02-05rwp | tcccgctgtGGGatgttgtgctgc | E02-05rmp | tcccgctgtGTGatgttgtgctgc |
| E02-08rwp | tggtatcgaccACCtcccgctgt | E02-08rmp | tggtatcgaccATCtcccgctgt |
| E02-10rwp | ttgggacaggTGGgactggttgag | E02-10rmp | ttgggacaggTAGgactggttgag |

Averages of spot intensities, PM/MM ratios, and coefficient of variations (CVs) were measured by testing 20 copies of chips according to a conventional method and 20 copies of chips according to hybridization system. The conditions for the processes are shown in Table 3.

TABLE 3

|  | Reference | | Hybstation method of present invention | |
|---|---|---|---|---|
|  | Spot intensity | Ratio | Spot intensity | Ratio |
| Average | 18438.55 | 2.52 | 9852.38 | 2.31 |
| CV | 32.78 | 7.05 | 13.66 | 4.69 |

Referring to Table 3, intensity CV and PM/MM ratio CV were much smaller when a hybridization system method according to an embodiment of the present invention was used than when a conventional reference method was used.

As mentioned above, in the hybridization system according to the present invention, the amount of the sample to be agitated for hybridization is very small, for example, about 45 ul. The construction of the hybridization system according to the present invention is inexpensive in comparison with conventional hybridization systems using pumps. In addition, only a pump and two valves are needed in order to perform agitation in a closed system such that the hybridization system according to the present invention can replace a conventional hybridization system using a Diaphragm pump or a conventional Peristaltic pump. Further, an undesired residual reaction product absorbed between a sealing pad and a chamber can be removed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A hybridization system for hybridizing a biochip comprising:
   a chamber device comprising at least a hybridization chamber including a support for a biochip and a first cover having a sample inlet;
   an agitation device comprising:
      two air channels connected to ends of the hybridization chamber;
      two valves disposed in the air channels;
      an integrated air channel to which the two air channels are connected; and
      an air pump disposed in the integrated air channel; and
   a washing and drying device comprising:
      a flow channel connected to one of the two air channels through a branched valve;
      a flow pump disposed in the flow channel; and
      a buffer inlet disposed opposite the flow channel.

2. The hybridization system of claim 1, further comprising a second cover including a cap which covers the sample inlet of the first cover.

3. The hybridization system of claim 2, further comprising an air vent formed in the side surface of an upper portion of the sample inlet contacting the cap or in the side surface of a lower portion of the cap contacting the sample inlet.

4. The hybridization system of claim 1, further comprising a sealing element that is integrated with a lower surface of the cover and surrounds the hybridization chamber.

5. The hybridization system of claim 4, wherein the sealing element comprises a protruding portion disposed inside the hybridization chamber and a recessed portion disposed outside the hybridization chamber.

6. The hybridization system of claim 1, further comprising a heater disposed below the hybridization chamber.

7. The hybridization system of claim 6, wherein the hybridization chamber is heated or cooled using a Peltier device.

8. The hybridization system of claim 1, wherein the sample inlet is disposed at the ends of the hybridization chamber and the air channels are connected to the ends of the hybridization chamber via side walls of the sample inlet.

9. The hybridization system of claim 1, wherein the air channel or the flow channel has a circular cross section and is formed by overlapping upper and lower substrates comprising grooves with a semi-circular cross section.

10. The hybridization system of claim 9, further comprising a sealing element that is integrated with the upper substrate or the lower substrate and surrounds the grooves of the upper substrate or the lower substrate.

11. The hybridization system of claim 10, wherein the sealing element comprises a protruding portion disposed inside the air channel or the flow channel and a recessed portion disposed outside the air channel or the flow channel.

12. The hybridization system of claim 1, wherein the valves of the agitation device are branched valves, which control a supply of air to a plurality of hybridization chambers.

13. The hybridization system of claim 1, further comprising an air line connected to the flow channel of the washing/drying device through the branched valve.

14. The hybridization system of claim 1, further comprising a branched valve which controls the supply of a plurality of buffers and is connected to a plurality of buffer inlets disposed opposite the flow channel of the washing/drying device.

15. The hybridization system of claim 1, further comprising:
   a computer CPU, which automatically controls opening and closing of the valves, operation of the pumps, and a temperature of a heater; and
   a monitor, which displays system operations.

* * * * *